United States Patent [19]

Turner et al.

[11] Patent Number: 4,923,580

[45] Date of Patent: May 8, 1990

[54] BROMINATION

[75] Inventors: Philip J. Turner, Cheshire, England; Martin Jeff, Houston, Tex.; Kevan M. Reeve, Cheshire, England

[73] Assignee: Interox Chemicals Limited, London, England

[21] Appl. No.: 326,065

[22] Filed: Mar. 20, 1989

[30] Foreign Application Priority Data

Mar. 19, 1988 [GB] United Kingdom ............... 8806582

[51] Int. Cl.$^5$ ............................................ B01J 19/08
[52] U.S. Cl. ........................... 204/157.97; 204/157.99; 204/158.1
[58] Field of Search ...................... 204/157.97, 157.99, 204/158.1

[56] References Cited

U.S. PATENT DOCUMENTS 4,165,268  8/1979  Marti .............................. 204/157.99
4,191,621  3/1980  Riethmann ..................... 204/157.99

FOREIGN PATENT DOCUMENTS 2187735  1/1974  France .
2370017  6/1978  France .
 118609  3/1976  German Democratic Rep. .
 130416  3/1978  German Democratic Rep. .
2004887  4/1979  United Kingdom .

*Primary Examiner*—John F. Niebling
*Assistant Examiner*—Ben C. Hsing
*Attorney, Agent, or Firm*—Larson and Taylor

[57] ABSTRACT

Selective bromination of alkylarenes to the alpha dibrominated derivative is desirable as a precursor for the selective production of, for example, the corresponding aromatic aldehyde.

Improvements in the extent of selectivity of the product and/or its rate of production can be obtained by employing a photolytic reaction between the substrate, hydrogen peroxide and hydrogen bromide using mole ratios of $H_2O_2$: substrate of about 2.8:1 or higher, preferably 3,2: to 3.5:1 and of bromide:substrate of over 2.5:1, preferably about 2.8:1 to 3.2:1 and progressive controlled introduction of the $H_2O_2$, the reaction being carried out in the presence of a substantial amount of an organic solvent, and preferably more than 5.5 volumes per volume of substrate, whilst irradiating with light preferably having principal emissions in the range of 250 to 600 nm. The reaction mixture is preferably maintained at 50° to 60° C. The reaction often takes from 5 to 12 hours, of which period hydrogen peroxide is introduced progressively into the reaction mixture during preferably the first 3 to 5 hours. The process is especially suitable for deactivated alkylarenes, such as o-nitrotoluene.

13 Claims, No Drawings

BROMINATION

The present invention relates to a process for the bromination of alkyl substituents of arenes and in particular to a process for the dibromination of such substituted arenes that contain additionally a deactivating substituent.

The inventors have recognised that it is possible to brominate an alkyl substituent of an arene at the alpha carbon atom, and especially methyl, by contacting the substrate with bromine whilst exposing the mixture to irradiation that is capable of generating free radicals of bromine. They have further recognised that bromination on the alkyl substituent can take place despite the presence around the arene nucleus of various other substituents such as in particular, strongly electron-withdrawing substituents, like nitro groups, which are capable of deactivating the substrate towards various substitution reactions when accordingly they might be expected to require more forcing conditions. Secondly, it has also been recognised that a bromine substituent itself tends to inhibit further bromination of an alkyl substituent, i.e. functions as a deactivating group, so that it becomes progressively more difficult to brominate a compound. Accordingly, it is potentially a severe test of a bromination system to dibrominate an arene substrate and particularly one that contains a deactivating group.

There is a further factor that has to be taken into account when determining what conditions might be appropriate to try in order to obtain the dibrominated compound reasonably selectively and that factor is the competition that could be expected from ionic reactions. These reactions would cause substitution of arene hydrogen atoms and would be expected to increase in importance as the concentration of bromine is increased. Naturally, if more forcing conditions for a reaction are needed, the increase in concentration of reagents springs to mind.

There has been a disclosure in East German Patent 130 416 to VEB Arzneimittelwerk Dresden that bromination of o-nitrotoluene can be carried out by first contacting the substrate (0.8 moles) with bromine (0.36 moles), irradiating the mixture with an infrared lamp providing heat and light, and when all the bromine had been consumed, generating further bromine in situ by gradual addition of hydrogen peroxide (0.36 moles) in order to continue the bromination process. Theoretically, such a procedure could result in the formation of 0.72 moles of monobrominated substrate, in the absence of any competetive reactions. The reactions were carried out in solution in carbon tetrachloride at reflux temperature of about 80° C. The yield of bromination product was 67% based on the bromine used and calculated as the monobromo product, which is about 0.48 moles. It can accordingly be deduced that the selectivity of the reaction was not very good, which suggests that other and competetive reactions were occurring to a very significant extent.

According to the present invention there is provided a process for the production of a brominated alkylbenzene substrate in an improved degree of selectivity to the dibrominated species in which process a dilute solution of the substrate in a non-reactive organic solvent is agitated with an aqueous phase containing over 2.5 moles of hydrogen bromide per mole of substrate and into which hydrogen peroxide is introduced progressively and in a controlled fashion in a mole ratio to the substrate of about 2.8:1 or higher, and the reaction mixture is maintained at a temperature in the range of about 20° to 80° C. and irradiated with light that is able to dissociate bromine into free radicals, until no substrate is detectable and no more than a minor proportion of monobrominated substrate remains.

By the employment of a process in which the four characteristics are combined of firstly a dilute solution of substrate, secondly employing high mole ratios of both hydrogen peroxide and hydrogen bromide to the substrate, thirdly by using bromine-dissociating irradiation and fourthly by the progressive and controlled introduction of the hydrogen peroxide, it is possible to improve the extent to which the substrate is reacted selectively to the dibrominated species, and/or the rate at which it is achieved.

The invention process is particularly suitable for the bromination at the alpha carbon atom in an alkyl substituent of deactivated benzene, i.e. benzene that is also substituted by a deactivating substituent such as cyano, sulpho and, especially, nitro substituents, and can also be employed for compounds in which the benzene ring is substituted by a fluoro, chloro, bromo or iodo group. The aforementioned non-alkyl substituent may be in any position around the benzene nucleus relative to the alkyl substituent, including in particular, the ortho position. The alkyl substituent is, particularly suitably, methyl. Thus, the present invention is described herein with particular reference to the bromination of ortho-nitrotoluene, but the conditions can be applied, with appropriate modifications, if needed, to the corresponding reactions employing the other deactivated substrates.

The reaction is carried out in the presence of an organic solvent which does not react to any significant extent with either hydrogen peroxide or bromine, such as chlorinated hydrocarbons, including specifically carbon tetrachloride, chloroform, methylene dichloride, ethylene dichloride, tetrachloroethylene and tetrachloroethane. The volume ratio of solvent to substrate, i.e. v/v, is often selected in the range of from over 5:1 to 15:1, preferably over 5.5:1, and good results have been achieved conveniently in the range of volume ratios of from 6:1 to 10:1, for example in conjunction with chloroform. By choosing a dilute solution compared with a more concentrated or very dilute solution, it is possible to obtain a comparatively high yield of dibrominated product within a given reaction period. Use of a more concentrated solution impairs the rate of reaction and the effective utilisation of the consumable reagents. However, at even higher extents of dilution, the benefits of improved reaction rate appear no longer to be obtained or to be offset by other factors such as reduced space yield. It will naturally be recognised by the skilled person that whilst the correlation between change in the rate and efficiency of the dibromination reaction with change in concentration of the substrate is of general applicability, the preferred range and extent of dilution to employ can also be dependent to some extent upon which solvent and which substrate is being employed.

One of the important characteristic features of the present invention process resides in the mole ratios of the reactants employed. The inventors found in the course of research into this class of reaction that the extent of bromination obtained is a function of the total amount of bromine that can be generated in situ and also a function of the ratio of hydrogen bromide and hydrogen peroxide. They recognised that it was necessary for both the hydrogen peroxide and the hydrogen bromide to be in excess of the theoretical amount of 2 moles per mole of substrate. In other words, and especially in the circumstances of a deactivated starting material that is further deactivated by the substitution of the first bromide group into the substrate, the addition of the second bromide substituent is very hard to achieve.

In practice, the mole ratio of hydrogen bromide to the substrate is often selected in the range of up to 3.5:1 and particularly good results have been obtained using a mole ratio of about 3:1 to substrate, a preferred range being 2.8:1 to 3.2:1. Although higher ratios may be employable, there is no perceived need and they can, in fact, seem to retard the rate of the bromination reaction at the same dilution extent of the substrate. To some extent, the retardation can be mitigated by employing a higher dilution, so that it is preferable and, in accordance with the foregoing findings, to select the extent of dilution in conjunction with the HBr:substrate ratio, the higher the ratio, the greater the extent of dilution. By way of example, it is desirable to employ the preferred HBr:substrate range of ratios (2.8 to 3.2:1) with a range of v/v dilutions of 6:1 to 10:1 for the organic solvent to substrate, whereas if a higher ratio of HBr:substrate such as about 3.5:1 is used, a range of dilutions that is correspondingly greater is preferred, namely about 8.5:1 to 15:1.

The hydrogen peroxide is preferably employed in a mole ratio to the substrate of up to 4:1 and especially in the preferred range of around 3.2:1 to 3.5:1. Use of a higher ratio of peroxide to substrate is economically wasteful and thus imprudent, though it is technically feasible. Use of the preferred range is particularly desirable in that it can achieve a balance between the desire to achieve selective dibromination with reasonable rapidity with the desire to minimise the amounts of reagents employed.

The hydrogen bromide and hydrogen peroxide are usually present in the aqueous solution. The hydrogen bromide can be introduced as such, for example as a concentrated aqueous solution, or produced in situ by acidification of a suitable soluble bromide salt or partly by reduction of bromine. The hydrogen peroxide is normally introduced into the reaction mixture in the form of a concentrated aqueous solution, such as from 35 to 70% w/w.

The radiation illuminating the reaction has as its object the dissociation of bromine into bromine radicals. Thus, the effective radiation has a wavelength of not more than 600 nm. A significant proportion of useful radiation is available from lamps which have principal emissions in the range of 600 to 250nm. Lamps which are described as daylight lamps have been found particularly suitable for the instant invention since the greater part of their radiation is emitted within the preferred wavelength range. Suitable lamps are often described as high pressure sodium discharge lamps (SON), mercury fluorescent lamps (MBF) and tungsten or tungsten halogen lamps. It is advantageous to filter out ultra-violet light, as happens, for example, when the radiation passes through "Pyrex" (Trademark) glass.

It will be recognised that there is a relationship between effective radiation intensity and reaction rate and consequently also with reaction period, the more intense the radiation, the faster the rate and shorter the reaction period needed to achieve the desired utilisation of the bromine reactant, employing a set of process conditions that otherwise remain the same. It will also be understood that the actual design of the apparatus employed will contribute significantly to the extent to which the radiation can be deployed effectively including external factors such as the distance of the light sources relative to reaction mixture. Radiation lamps can for example be positioned above the surface of the reaction mixture and/or immersed within it. Alternatively or additionally the vessel can be provided with translucent ports through which the radiation is shone into the reaction mixture. Reflectors can be used to minimise radiation losses. By way of guidance only, we have found that at the laboratory bench scale of working, it is convenient to employ one or two daylight spectrum lamps each having a nominal luminous flux of 8500 lumens set at a distance of about 20/25 cms from and pointing towards the reaction vessel or closer, which permits the reaction to progress to completion or near completion within a working day.

It is of practical importance to take into account internal factors that affect the efficiency of utilisation of the radiation employed, when designing more suitable reaction vessels for this reaction. These factors include the ratio of reaction volume to illuminated surface area and the maximum effective path length of the radiation in the reaction mixture, which will itself correlate with the concentrations of light absorbers in the mixture. The interaction between the two factors determines the proportion of reaction volume that is effectively illuminated at any time. As the proportion falls away from 100% of the volume, the reaction time tends to lengthen. The actual design of the reaction vessel is within the control of the process operator and in preference the apparatus will be selected or modified so as to minimise or eliminate volumes of reaction mixture that are not penetrated by the radiation directly, or will employ preferably efficient mixing of the reaction mixture so as to increase the likelihood of all the reaction mixture containing bromine and substrate passing frequently through an illuminated zone of the reaction vessel.

The total reaction period for the reaction comprises normally two parts, namely the period of introduction of the hydrogen peroxide and secondly the post-introduction period. It is convenient to employ an introduction period selected in the region of 60 to 360 minutes during which period peroxide is introduced progressively, such as continuously or in small amounts quite regularly, although a longer period of introduction can be used if desired, in which case the post-introduction period would usually be correspondingly shorter. The rate of introduction of the peroxide is, very desirably, controlled in conjunction with the other process parameters and in particular those which strongly influence the rate of consumption of bromine in order to keep to acceptably low levels the proportion of peroxide lost by decomposition. The control the rate of bromine production, which occurs as a direct result of progressive introduction of the hydrogen peroxide, means that there is control of the concentration of bromine in the reaction mixture to levels that are substantially lower than would be the case if all the bromine were introduced as such. In consequence, the invention process is able to avoid to a considerable extent the physical bromine losses that could otherwise result from a prolonged reaction period at elevated temperatures, and additionally circumvents excessive retardation of the reaction that could arise from the presence of over 2 moles of bromine per mole of substrate in the reaction mixture that would be needed to obtain the dibromo compound. The extent of peroxide losses tends to increase as the rate of peroxide addition becomes excessively fast, and thus the benefits of the invention can become dissipated or further peroxide addition is needed. Where the other process parameters are comparatively favourable to an overall rapid production of the dibromo compound, the rate of peroxide introduction can be varied over all or at least most of the above range whereas when the other process parameters are less favourable, the periods of peroxide introduction at or towards the upper fraction of the above-identified range, such as 180 to 360 minutes are distinctly preferable.

The reaction may be allowed to continue until all the bromine generated in situ has been consumed, which is shown by a loss or change of colour in the reaction mixture or, more conveniently, samples of the reaction mixture can be extracted at appropriate intervals and analysed for the substrate and particularly for its mono and dibrominated derivatives, the reaction being halted when the proportion of monobrominated substrate has fallen to below a preset amount, such as a figure in the range of 10 to 5 molar % or lower. A reaction period determined in such a manner can be employed subsequently without such elaborate analyses being employed during the reaction, except by way of confirmation at the end. In many instances, the total reaction period lasts from 4 to 12 hours, depending at least in part upon the temperature and design of apparatus employed and also taking into account the mole ratios of the reagents and the extent of dilution of the reaction mixture. By way of further guidance, the substrate will be consumed under most if not all of the reaction conditions of the instant invention before the desired extent of production of the dibrominated product has been obtained.

Whilst the temperature of the reaction process may be chosen within the aforementioned range, it is preferred to employ a temperature of from 50° to 60° C. in conjunction with chloroform as the diluting inert solvent. Naturally, in conjunction with selection of a higher reaction temperature, a higher boiling point solvent of the type described herein is correspondingly selected at the same time.

At the end of the reaction period, the aqueous and non-aqueous phases can be separated, and the desired product is retained in the non-aqueous phase. The phase can be washed with a dilute alkaline solution to remove alkali-soluble impurities. Solvent can be removed from the solution under vacuum and solid products crystallised out. If desired, the monobrominated derivative can be separated by recrystallisation, for example from an alcoholic solution, but advantageously, further processing of the product, such as hydrolysis to the corresponding aromatic aldehyde, can be effected without an intermediate purification step. The aqueous phase, which still contains some residual hydrogen bromide can be retained and, if desired, can be concentrated for subsequent reuse.

Having described the reaction in general terms, specific embodiments will hereafter be described more fully by way of example only.

COMPARISONS CA TO CE AND EXAMPLES 1 to 3

In the comparisons and Examples, the same apparatus was employed and the same experimental procedure was followed, the principal differences residing in the selection of the components of the reaction mixture.

The apparatus comprised a multi-necked 500 ml glass-flask equipped with stirrer, thermometer, reflux condenser and inlet port for the introduction of reagents, held in a water-bath to effect temperature control. The flask was illuminated by a daylight spectrum lamp, specifically either a Thorn A1/258 24 volt 250 watt lamp having nominal luminous flux of 8500 lumens or a 500 watt tungsten halogen open face floodlamp having nominal luminous flux of 9500 lumens, that was positioned at a distance of about 20cms away from the flask. Standardisation trials on Example 2 showed that the two lamps gave virtually indistinguishable results under otherwise identical process conditions, despite the apparent difference of 1000 lumens.

The experimental method comprised introducing ortho-nitro toluene, 0.4 moles, referred to as ONT in the Tables and all the non-reactive diluent, chloroform, into the flask, introducing all the hydrogen bromide as a 50% w/w solution in water, heating the mixture to reflux, about 54° C. and thereafter introducing aqueous hydrogen peroxide in the form of 65% w/w solution gradually over a period of about 4 hours. The reaction mixture was thereafter maintained at the reaction temperature whilst being well-stirred during the reaction period, samples periodically being taken and analysed by glc and hplc to check upon the progress of the reaction. The reaction was halted by switching off the illumination and cooling the mixture, either when loss of colour from the reaction mixture, which indicated that all the bromine had been consumed or at the end of one day's total reaction time, which was 8 hours, approximately, whichever occurred first. The final mixture analysed by glc/hplc to determine the extent of reaction, and the amounts of the desired product, ortho-nitro benzal bromide abbreviated to DB and the non-desired ortho-nitro benzyl bromide, which is abbreviated to MB. The analysis showed that complete conversion of the substrate to the two products had been achieved for all the Comparisons and Examples. The selectivity of the reaction is accordingly given by the ratio of MB:DB, which is specified in the Table below. The results given for Example 2 are the average of many runs, the overall range being about +/−3% for each product.

TABLE 1

| Ex/Comp | Mole ratio of Reactants | | | Solvent mls | % Yield | |
|---|---|---|---|---|---|---|
| | HBr | H$_2$O$_2$ | ONT | | MB | DB |
| CA | 2.0 | 2.2 | 1 | 400 | 59 | 41 |
| CB | 2.0 | 2.8 | 1 | 400 | 24 | 76 |
| CC | 2.0 | 3.2 | 1 | 300 | 38 | 62 |
| CD | 2.5 | 3.2 | 1 | 300 | 21 | 79 |
| CE | 3.0 | 2.5 | 1 | 300 | 48 | 52 |
| 1 | 3.0 | 2.8 | 1 | 400 | 8 | 92 |
| 2 | 3.0 | 3.2 | 1 | 300 | 5 | 95 |
| 3 | 3.5 | 3.5 | 1 | 300 | 10 | 90 |

From Table 1, it can be seen that when a mole ratio of HBr and H$_2$O$_2$ to ONT is employed that is close to the theoretical ratio of 2:2:1, the result is that only a minor proportion of ortho-nitro benzal bromide, the desired product, is obtained. Increasing only one of the two reactants to a mole ratio to the ONT to around 3:1 offers some improvement in the selectivity of production of the desired product, as can be seen from results CB to CD, it is necessary for both to be around 3:1 or higher before a reasonably acceptably selective production of the dibrominated product is obtained.

EXAMPLES 4 to 6

In these Examples, the reaction conditions of Example 2 was followed with two exceptions. Firstly, the distance of the lamps from the reaction vessel was altered to the distances given in Table 2, which summarises the results. Secondly, the reaction was permitted to continue until the hplc analysis of periodically taken samples showed that the molar ratio of the dibrominated product to monobrominated product had exceeded the ratio of 90:10. The overall reaction time until then is recorded as the reaction time. In the Examples, whenever the experimental technique required a reaction period substantially in excess of 8 hours, as was the case for Example 4, the reaction mixture was cooled to ambient temperature after 8 hours and stored in the dark overnight and the reaction restarted the following morning by rapid reheating and by switching on the illumination. In Example 6, two lamps were used, each at the same distance from the vessel.

TABLE 2

| Example No. | Lamp to Reactor Distance (cm) | Reaction Time (hours) |
|---|---|---|
| 4 | 30 | 15 |
| 5 | 2 | 8 |
| 6 | 2 | 5 |

From Table 2, it can be seen that the effect of increasing the illuminance, either by bringing the lamp closer or by increasing the number of lamps, is to increase the rate of producing the dibrominated compound.

COMPARISONS CF AND CG AND EXAMPLES 7 and 8

In these Comparisons and Examples, the general procedure of Example 2 was followed, except that the v/v ratio of chloroform diluent to substrate (ortho nitro toluene) was that given in Table 3 below, and the reaction was permitted to continue for longer than 8 hours, the actual permitted period and product analysis being summarised in Table 3, below.

TABLE 3

| Comparison/ Example No | V/V ratio | Reaction Time (hours) | % Yield MB | % Yield DB |
|---|---|---|---|---|
| CF | 4.2:1 | 15.5 | 62 | 38 |
| CG | 5.0:1 | 14.0 | 39 | 61 |
| 7 | 6.4:1 | 10.0 | 2 | 98 |
| 8 | 8.5:1 | 11.5 | 7 | 93 |

From Table 3, it can be seen that the effect of diluting the reaction mixture is to promote the extent and rate of selective production of the dibrominated product. Thus, not only is the rate of reaction accelerated, as seen by a comparison of the reaction times, despite the fact that the illumination of the reaction vessel was the same for all four experiments, but the proportions of the two products differed markedly, depending directly upon the extent of substrate dilution.

EXAMPLES 9 and 10

In these Examples, the procedure of Example 2 was followed, with the exception that the rate of introduction of hydrogen peroxide was as shown in Table 4 below and the reaction was halted after a total of 7 hours reaction time. It was observed that gas was evolved during the course of Example 9, which indicated that some of the peroxide was decomposing before it could react with hydrogen bromide.

TABLE 4

| Example No | Peroxide Addition (hours) | % Yield MB | % Yield DB |
|---|---|---|---|
| 9 | 2 | 27 | 73 |
| 10 | 4 | 8 | 92 |

From Table 4, it can be seen that the effect of adding the hydrogen peroxide more quickly, as in Example 9, was to impair the extent of conversion of the substrate to the desired dibrominated compound within the given reaction period of 7 hours, and that when a greater degree of control is exercised, as in Example 10, the production of the dibrominated compound is more favoured.

EXAMPLE 11

In this Example, the procedure of Example 2 was repeated, with the exceptions that the mole ratio of hydrogen bromide to substrate had been increased to 3.5:1, the organic solvent was present in v/v ratio to the substrate of 10:1 and two lamps were used, each at a distance of 2 cms from the vessel. The molar yield of product was measured at the end of 6.25 hours total reaction period, and was found to consist of 6% of monobrominated product MB and 94% of dibrominated product DB. This result indicates clearly that a retardation in the rate of the reaction attributable to an increased concentration of HBr in the mixture can be ameliorated or overcome by increasing the extent of dilution of the organic phase, and increasing the illuminance.

We claim:

1. A process for the production of a dibrominated alkylbenzene product from an alkylbenzene substrate in which process in step (a) a dilute solution of the substrate in a non-reactive organic solvent is agitated with an aqueous phase containing over 2.5 moles of hydrogen bromide per mole of substrate and
    in step (b) (i) hydrogen peroxide which generates bromine from the hydrogen bromide, is introduced progressively and in a controlled manner into the mixture obtained in step (a) in a mole ratio to the substrate of about 2.8:1 or higher, and (ii) the mixture is maintained at a temperature in the range of about 20° to 80° C. and irradiated with light that is able to dissociate the bromine into free radicals, until no substrate is detectable and no more than a minor proportion of monobrominated substrate remains.

2. A process according to claim 1 in which the mole ratio of bromide to substrate is in the range of 2.8:1 to 3.2:1.

3. A process according to claim 1 in which the mole ratio of hydrogen peroxide to substrate is selected in the range of from 3:1 to 3.5:1.

4. A process according to claim 1 in which the organic solvent is present in a v/v ratio to the substrate of over 5.5:1.

5. A process according to claim 4 in which the organic solvent is present in a v/v ratio to the substrate of from 6:1 to 10:1.

6. A process according to claim 4 in which the extent of dilution of the substrate by the organic solvent is selected in conjunction with the ratio of hydrogen bromide to substrate, the higher the ratio, the proportionately greater the extent of dilution.

7. A process according to claim 1 in which the mixture is irradiated with light that is free from ultra-violet light or from which the ultra-violet light has been filtered out before entering the reaction mixture.

8. A process according to claim 1 in which step (b) is continued until at least 90 mole % of the substrate has been converted to the dibrominated product.

9. A process according to claim 1 in which hydrogen peroxide is introduced continuously or in small increments during a period of at least 180 minutes.

10. A process according to claim 1 in which step (b) is carried out for a period of time in the range of 4 to 12 hours and the irradiation maintained and wherein the process is carried out in apparatus so designed as to achieve at least 90 mole % conversion to the dibrominated product therewithin.

11. A process according to claim 1 in which the organic solvent is a chlorinated hydrocarbon.

12. A process according to claim 1 in which the reaction is conducted at a temperature of from 50° to 60° C.

13. A process according to claim 1 in which the substrate is toluene substituted by a deactivating group selected from the group consisting of cyano, nitro and sulpho groups.

* * * * *